US009665950B2

(12) United States Patent
Kiyohara (10) Patent No.: US 9,665,950 B2
(45) Date of Patent: May 30, 2017

(54) X-RAY IMAGING SYSTEM AND IMAGE PROCESSING DEVICE

(71) Applicant: Konica Minolta, Inc., Chiyoda-ku, Tokyo (JP)

(72) Inventor: Junko Kiyohara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 126 days.

(21) Appl. No.: 14/819,725

(22) Filed: Aug. 6, 2015

(65) Prior Publication Data
US 2016/0042533 A1 Feb. 11, 2016

(30) Foreign Application Priority Data

Aug. 6, 2014 (JP) ................................. 2014-160428

(51) Int. Cl.
| | |
|---|---|
| *G06K 9/00* | (2006.01) |
| *G06T 11/00* | (2006.01) |
| *G01N 23/20* | (2006.01) |
| *A61B 6/00* | (2006.01) |
| *G01N 23/04* | (2006.01) |

(52) U.S. Cl.
CPC ............ *G06T 11/00* (2013.01); *A61B 6/4291* (2013.01); *A61B 6/484* (2013.01); *A61B 6/5205* (2013.01); *G01N 23/04* (2013.01); *G01N 23/20075* (2013.01); *G06T 2207/10116* (2013.01); *G21K 2201/067* (2013.01)

(58) Field of Classification Search
None
See application file for complete search history.

(56) References Cited

U.S. PATENT DOCUMENTS

| | | | | |
|---|---|---|---|---|
| 2010/0080436 A1* | 4/2010 | Ohara | ...................... | A61B 6/06 382/132 |
| 2011/0243305 A1* | 10/2011 | Tada | .................... | A61B 6/4291 378/87 |
| 2012/0153182 A1* | 6/2012 | Iwakiri | ................ | A61B 6/4283 250/394 |
| 2012/0163537 A1* | 6/2012 | Iwakiri | ................ | A61B 6/4283 378/62 |
| 2012/0224670 A1* | 9/2012 | Kiyohara | ................. | A61B 6/06 378/62 |

(Continued)

FOREIGN PATENT DOCUMENTS

WO 2012057022 A1 5/2012

*Primary Examiner* — Avinash Yentrapati
(74) *Attorney, Agent, or Firm* — Cantor Colburn LLP (57) ABSTRACT

An X-ray imaging system includes an X-ray imaging device and an image processing device including a reconstruction unit and an estimation unit. The X-ray imaging device uses a Talbot or Talbot-Lau interferometer including gratings disposed in a line. The X-ray imaging device obtains sets of moire fringe images by fringe scanning multiple times between which arrangement of the gratings is changed. In the fringe scanning, one of the gratings is moved relatively to the remaining grating. The reconstruction unit generates, on the basis of the sets, a reconstructed image which is a differential phase image, an X-ray absorption image and/or a small-angle scattering image. The estimation unit estimates, on the basis of the reconstructed image, a relative position of the moved grating from a reference position of the grating at each imaging in the fringe scanning.

8 Claims, 6 Drawing Sheets

(56) References Cited

U.S. PATENT DOCUMENTS

| | | | |
|---|---|---|---|
| 2012/0250972 A1* | 10/2012 | Tada | A61B 6/4291 382/132 |
| 2012/0281217 A1* | 11/2012 | Ouchi | A61B 6/06 356/432 |
| 2013/0011040 A1* | 1/2013 | Kido | A61B 6/4291 382/132 |
| 2013/0083893 A1* | 4/2013 | Ishii | A61B 6/484 378/62 |
| 2013/0142308 A1* | 6/2013 | Ishii | G01N 23/04 378/62 |
| 2013/0201198 A1* | 8/2013 | Nagatsuka | A61B 6/463 345/581 |
| 2013/0308750 A1* | 11/2013 | Ishii | A61B 6/4233 378/36 |
| 2013/0314714 A1* | 11/2013 | Nagai | G01B 9/02 356/451 |
| 2014/0010344 A1* | 1/2014 | Nagatsuka | A61B 6/06 378/37 |
| 2014/0146945 A1* | 5/2014 | Fredenberg | A61B 6/4233 378/62 |
| 2014/0198895 A1* | 7/2014 | Hoshino | A61B 6/482 378/36 |
| 2014/0286475 A1* | 9/2014 | Nakamura | G01T 1/16 378/51 |
| 2016/0324496 A1* | 11/2016 | Fredenberg | A61B 6/06 |

* cited by examiner

DIFFERENTIAL PHASE IMAGE

FIG.10

| X-RAY ABSORPTION IMAGE | SMALL-ANGLE SCATTERING IMAGE | DIFFERENTIAL PHASE IMAGE |
|---|---|---|
|  |  |  |

X-RAY IMAGING SYSTEM AND IMAGE PROCESSING DEVICE

CROSS-REFERENCE TO RELATED APPLICATIONS

This application is based upon and claims the benefit of priority under 35 U.S.C. 119 of Japanese Patent Application No. 2014-160428 filed Aug. 6, 2014, the entire disclosure of which, including the specification, claims, drawings and abstract, is incorporated herein by reference in its entirety.

FIELD OF THE INVENTION

The present invention relates to an X-ray imaging system and an image processing device.

DESCRIPTION OF THE RELATED ART

In order to obtain a high-resolution image with an X-ray imaging device with a Talbot interferometer or Talbot-Lau interferometer, there is used a fringe scanning method of performing imaging M times (M is a positive integer of more than 2) while moving one of gratings 1/M of a slit interval of the grating in a slit interval direction each time imaging is performed, and reconstruction is performed with the images (moire fringe images) obtained thereby. However, the slit interval of a grating is about 20 μm at the largest, so that the movement amount of the grating per time in fringe scanning is 1 μm order. Therefore, the position of the grating at each of M times imaging is performed needs to be decided with an accuracy of 0.01 μm order (1% or less of the slit interval).

When each imaging is performed with error in the position of the grating, measured physical quantities have error and also a reconstructed image(s) generated on the basis of the taken moire fringe images has unevenness therein, which is undesirable.

Then, for example, there is described in International Patent Application Publication No. 2012/057022 a technique to prevent image degradation due to error in the position of a grating by measuring the position of the grating with a sensor or the like and reflecting the measured position on a parameter used in a reconstruction process.

However, in the technique described in International Patent Application Publication No. 2012/057022, a special sensor which can measure the position of a grating at 0.01 μm order needs to be added to an X-ray imaging device, which is costly.

BRIEF SUMMARY OF THE INVENTION

Objects of the present invention include preventing, at low cost, image degradation due to error in a relative position of a grating moved in fringe scanning without adding a special sensor to detect the relative position of the grating to an X-ray imaging device.

In order to achieve at least one of the objects, according to an aspect of the present invention, there is provided an X-ray imaging system including: an X-ray imaging device with a Talbot interferometer or Talbot-Lau interferometer in which a plurality of gratings are disposed in a line in an X-ray emitting direction and which obtains moire fringe images by fringe scanning in which one of the gratings is moved relatively to the remaining grating, each of the gratings including a plurality of slits disposed in a direction perpendicular to the X-ray emitting direction; and an image processing device including a reconstruction unit which generates at least one of a differential phase image, an X-ray absorption image and a small-angle scattering image as a reconstructed image on the basis of the moire fringe images obtained by the X-ray imaging device, wherein the x-ray imaging device obtains multiple sets of moire fringe images by the fringe scanning multiple times between which arrangement of the gratings is changed, the reconstruction unit of the image processing device generates a reconstructed image on the basis of the sets of the moire fringe images obtained by the x-ray imaging device, and the image processing device further includes an estimation unit which estimates, on the basis of the reconstructed image generated by the reconstruction unit, a relative position of the moved grating from a reference position of the grating at each imaging in the fringe scanning.

According to another aspect of the present invention, there is provided an image processing device including: a reconstruction unit which generates at least one of a differential phase image, an X-ray absorption image and a small-angle scattering image as a reconstructed image on the basis of moire fringe images obtained by an X-ray imaging device with a Talbot interferometer or Talbot-Lau interferometer in which a plurality of gratings are disposed in a line in an X-ray emitting direction and which obtains the moire fringe images by fringe scanning in which one of the gratings is moved relatively to the remaining grating, each of the gratings including a plurality of slits disposed in a direction perpendicular to the X-ray emitting direction; and an estimation unit which estimates, on the basis of a reconstructed image generated by the reconstruction unit on the basis of multiple sets of moire fringe images obtained by the X-ray imaging device by the fringe scanning multiple times between which arrangement of the gratings is changed, a relative position of the moved grating from a reference position of the grating at each imaging in the fringe scanning.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein.

DETAILED DESCRIPTION OF THE INVENTION

[Configuration of X-Ray Imaging System]

Hereinafter, an embodiment of the present invention is described with reference to the drawings.

Figure 1:
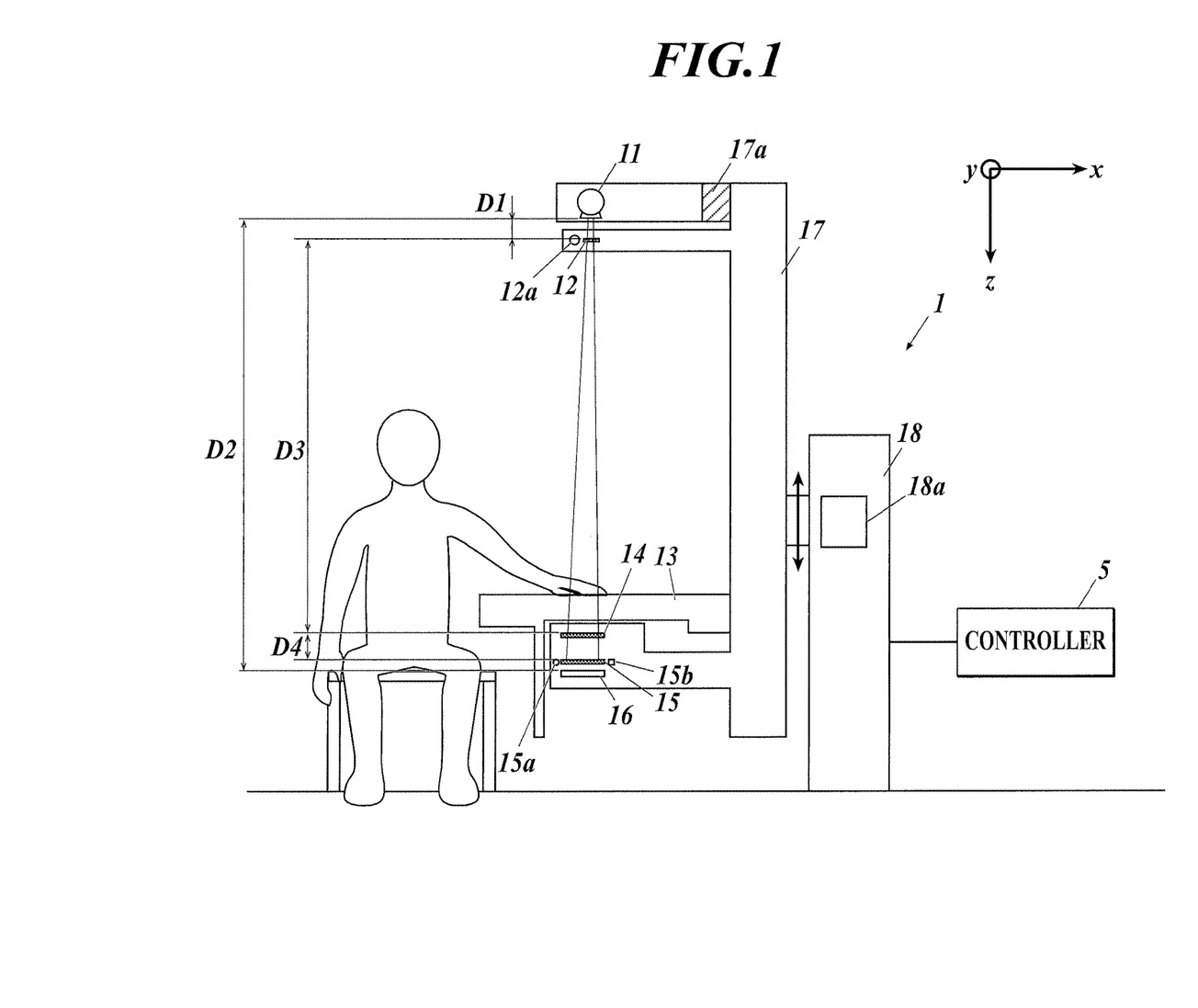
FIG. 1 shows the overall configuration of an X-ray imaging system as an embodiment of the present invention.

FIG. 1 shows an example of the configuration of an X-ray imaging system as an embodiment. The X-ray imaging system includes an X-ray imaging device 1 and a controller 5. The X-ray imaging device 1 performs X-ray imaging (fringe scanning) with a Talbot-Lau interferometer, and the controller 5 generates reconstructed images of a subject using a plurality of moire fringe images obtained by the X-ray imaging.

The X-ray imaging device 1 includes, as shown in FIG. 1, an X-ray source 11, a multi-slit (source grating) 12, a subject table 13, a first grating 14, a second grating 15, an X-ray detector 16, a support unit 17 and a main body unit 18.

The X-ray imaging device 1 is a vertical type, and the X-ray source 11, the multi-slit 12, the subject table 13, the first grating 14, the second grating 15 and the X-ray detector 16 are arranged in this order in the gravity direction which is in a Z direction. D1 (mm) represents distance between the focal point of the X-ray source 11 and the multi-slit 12, D2 (mm) represents distance between the focal point of the X-ray source 11 and the X-ray detector 16, D3 (mm) represents distance between the multi-slit 12 and the first grating 14, and D4 (mm) represents distance between the first grating 14 and the second grating 15. The subject table 13 may be positioned between the first grating 14 and the second grating 15.

The distance D1 is preferably 5 mm to 500 mm and far preferably 5 mm to 300 mm.

The distance D2 is preferably 3,000 mm or less because the height of an X-ray room is about 3 m or less in general. The distance D2 is far preferably 400 mm to 3,000 mm and still far preferably 500 mm to 2,000 mm.

The distance (D1+D3) between the focal point of the X-ray source 11 and the first grating 14 is preferably 300 mm to 3,000 mm and far preferably 400 mm to 1,800 mm.

The distance (D1+D3+D4) between the focal point of the X-ray source 11 and the second grating 15 is preferably 400 mm to 3,000 mm and far preferably 500 mm to 2,000 mm.

As these distances, optimum distances with which a grating image (self-image) of the first grating 14 lies on the second grating 15 may be calculated and set from the wavelength of X-rays emitted from the X-ray source 11.

The X-ray source 11, the multi-slit 12, the subject table 13, the first grating 14, the second grating 15 and the X-ray detector 16 are all supported by the support unit 17, and a positional relationship thereof in the z direction is fixed. The support unit 17 is formed in an arm shape and attached to the main body unit 18 to be movable in the z direction through a drive unit 18a provided in the main body unit 18.

The X-ray source 11 is supported through a buffer member 17a. The buffer member 17a may be formed of any material as long as it can absorb shocks and vibrations. Examples thereof include an elastomer. The X-ray source 11 emits X-rays and thereby generates heat. Hence, the material of a part of the buffer member 17a, the part being close to the X-ray source 11, is preferably heat-insulating too.

The X-ray source 11 includes an X-ray tube, and generates X-rays with the X-ray tube and emits the X-rays in the gravity direction (z direction). As the X-ray tube, for example, a Coolidge X-ray tube or a rotating anode X-ray tube widely and generally used at medical sites can be used. For the anode, tungsten or molybdenum can be used.

The diameter of the focal point of the X-ray source 11 (X-ray tube) is preferably 0.03 mm to 3 mm and far preferably 0.1 mm to 1 mm.

In an X-ray emitting direction of the X-ray source 11, a not-shown irradiation field diaphragm to narrow an irradiated area with X-rays is provided.

Figure 2:
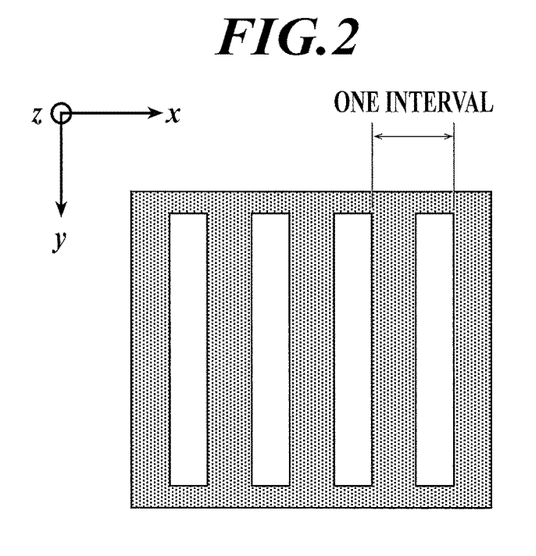
FIG. 2 is a plan view of a multi-slit.

The multi-slit 12 is a diffraction grating in which slits are arranged at predetermined intervals in an x direction as shown in FIG. 2. The multi-slit 12 is formed of a material having a large X-ray shielding force, namely, a material having a high X-ray absorption factor, such as tungsten, lead or gold, on a substrate made of a material having a low X-ray absorption factor, such as silicon or glass. The multi-slit 12 is formed, for example, by using photolithography by which a resist layer is masked in the shape of slits and irradiated with UV, so that the slit pattern is transferred to the resist layer. The slit structure having the same shape as the pattern is obtained by the exposure, and metal is embedded in the slit structure by electroforming. Thus, the multi-slit 12 is formed.

The slit interval of the multi-slit 12 is 1 μm to 60 μm. The slit interval (one interval) is, as shown in FIG. 2, distance between slits adjacent to each other. The slit width (length in the x direction) is 1% to 60% of the slit interval, preferably 10% to 40% thereof. The slit height (length in the z direction) is 1 μm to 500 μm, preferably 1 μm to 150 μm.

The slit interval of the multi-slit 12 can be obtained by the following formula, wherein $w_0$ (μm) represents the slit interval of the multi-slit 12, and $w_2$ (μm) represents the slit interval of the second grating 15.

$$w_0 = w_2 \cdot D3/D4$$

By determining the slit interval $w_0$ in such a way as to satisfy the formula, self-images formed by the X-rays passing through the slits of the multi-slit 12 and the first grating 14 are superimposed on the second grating 15. This state is what is called "in focus".

The subject table 13 is where a subject is placed and provided at a subject placement position on a path of X-rays (X-ray path) emitted from the X-ray source 11.

The first grating 14 is, as with the multi-slit 12, a diffraction grating in which slits are arranged at predetermined intervals in the x direction (see FIG. 2). The first grating 14 can be formed by photolithography with UV as with the multi-slit 12 or may be formed by what is called ICP with which fine lines are deeply drilled in a silicon substrate, whereby the grating structure is formed of silicon only. The slit interval of the first grating is 1 μm to 20 μm. The slit width is 20% to 70% of the slit interval, preferably 35% to 60% thereof. The slit height is 1 μm to 100 μm.

In the case where the first grating 14 used is a phase grating, the slit height is made to be a height with which a phase difference due to two types of materials forming the slit interval, namely, a material of an X-ray transmitting part and a material of an X-ray shielding part, becomes π/8 to 15×π/8, preferably π/2 or π. In the case where the first grating 14 used is an absorption grating, the slit height is made to be a height with which the X-ray shielding part sufficiently absorbs X-rays.

In the case where the first grating 14 used is a phase grating, the distance D4 between the first grating 14 and the second grating 15 needs to substantially satisfy the following condition, wherein $w_1$ (μm) represents the slit interval of the first grating 14.

$$D4 = p \cdot (w_1^2/\lambda) \cdot \{D3/(D3 - p \cdot w_1^2/\lambda)\}$$

In the formula, p represents a Talbot order, and when the height of the first grating 14 corresponds to a phase difference of π/2, p=n/2, whereas when the height thereof corresponds to a phase difference of π, p=n/8 (n is a positive odd number). In addition, λ in the formula represents the wavelength of X-rays.

The second grating 15 is, as with the multi-slit 12, a diffraction grating in which slits are arranged at predetermined intervals in the x-direction (see FIG. 2). The second grating 15 can also be formed by photolithography. The slit interval of the second grating 15 is 1 μm to 20 μm. The slit width is 30% to 70% of the slit interval, preferably 35% to 60% thereof. The slit height is 1 μm to 100 μm. The grating planes of the first grating 14 and the second grating 15 are perpendicular to the z-direction (parallel in the x-y plane).

As shown in FIG. 1, adjacent to the second grating 15, a drive unit 15a is provided. The drive unit 15a moves the second grating 15 in the x direction which is the slit interval direction. As the drive unit 15a, a drive mechanism (s) having a relatively large speed reduction ratio, such as a worm gear speed reducer, can be used alone or in combination.

In the embodiment, near the second grating 15, a relative angle adjustment unit 15b is provided to adjust a relative angle θ of the second grating 15 to the first grating 14 (a relative angle thereof in the x-y plane).

The multi-slit 12, the first grating 14 and the second grating 15 can be configured, for example, as described below.

X-ray Source 11: Diameter of Focal Point; 300 μm, Tube Voltage; 40 kVp, Added Filter; aluminum and 1.6 mm Distance D1 from Focal Point of X-ray Source 11 to Multi-slit 12: 240 mm Distance D3 from Multi-slit 12 to First Grating 14: 1,107 mm Distance D3+D4 from Multi-slit 12 to Second Grating 15: 1,364 mm Multi-slit 12: Size; 10 mm square, Slit Interval; 22.8 μm First Grating 14: Size; 50 mm square, Slit Interval; 4.3 μm Second Grating 15: Size; 50 mm square, Slit Interval; 5.3 μm In the X-ray detector 16, conversion elements which generate electric signals according to the amounts of the X-rays with which the conversion elements are irradiated are two-dimensionally arranged. The X-ray detector 16 reads the electric signals generated by the conversion elements as image signals.

The pixel size of the X-ray detector 16 is preferably 10 μm to 300 μm and far preferably 50 μm to 200 μm.

It is preferable that the X-ray detector 16 be fixed to the support unit 17 in such a way as to contact the second grating 15. This is because, the larger the distance between the second grating 15 and the X-ray detector 16 is, the more the moire fringe images obtained by the X-ray detector 16 are blurred.

As the X-ray detector 16, an FPD (Flat Panel Detector) can be used. There are an indirect conversion type FPD, with which detected X-rays are converted into electric signals through photo-electric conversion elements, and a direct conversion type FPD, with which detected X-rays are directly converted into electric signals. Either of them can be used.

The indirect conversion type FPD is configured in such a way that, under a scintillator plate made of CsI, $Gd_2O_2S$ or the like, photo-electric conversion elements associating with TFTs (Thin Film Transistors) are two-dimensionally arranged, thereby constituting pixels. When absorbing the X-rays entering the X-ray detector 16, the scintillator plate emits light. The photo-electric conversion elements convert this emitted light into electric charges and accumulate the electric charges therein. The accumulated electric charges are read out as image signals.

The direct conversion type FPD is configured in such a way that an amorphous selenium film, having a film thickness of 100 μm to 1,000 μm, is formed on glass by thermal deposition of amorphous selenium, and the amorphous selenium film and electrodes are vapor-deposited on an array of TFTs which are two-dimensionally arranged. When the amorphous selenium film absorbs X-rays, voltage is released into the substance in the form of electron-hole pairs, and the TFTs read out voltage signals between the electrodes.

As the X-ray detector 16, an imager such as a CCD (Charge Coupled Device) or an X-ray camera may be used.

Figure 3:
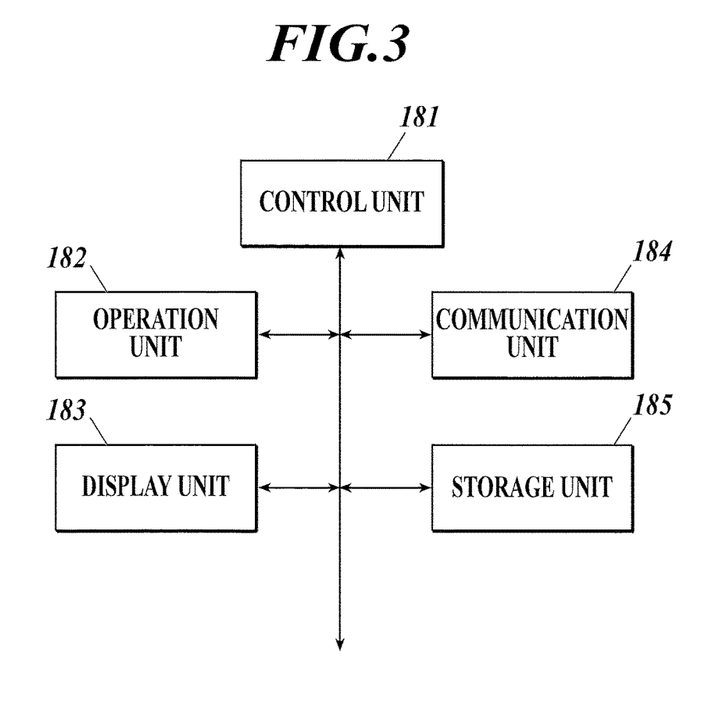
FIG. 3 is a block diagram showing the functional configuration of a main body unit.

The main body unit 18 includes, as shown in FIG. 3, a control unit 181, an operation unit 182, a display unit 183, a communication unit 184 and a storage unit 185.

The control unit 181 includes a CPU (Central Processing Unit) and a RAM (Random Access Memory) and performs a fringe scanning control process by working together with a program stored in the storage unit 185. More specifically, the control unit 181 is connected with the X-ray source 11, the drive unit 15a, the drive unit 18a, the X-ray detector 16 and so forth and controls, for example, movement of the second grating 15, timing of and conditions for emitting X-rays from the X-ray source 11, and timing of reading image signals with the X-ray detector 16.

The operation unit 182 includes an exposure switch, and generates operation signals in response to the exposure switch and so forth being operated and outputs the operation signals to the control unit 181.

The display unit 183 displays, on its display, operation screens, action statuses of the X-ray imaging device 1 and so forth under display control of the control unit 181.

The communication unit 184 includes a communication interface and communicates with the controller 5 on a network. For example, the communication unit 184 sends moire fringe images to the controller 5, the moire fringe images being read by the X-ray detector 16 and stored in the storage unit 185.

The storage unit 185 stores therein programs which are executed by the control unit 181, data necessary for execution of the programs, process results obtained by execution of the programs and so forth. The storage unit 185 also stores therein the moire fringe images obtained by the X-ray detector 16.

The controller 5 is an image processing device which generates reconstructed images of a subject using a series of moire fringe images obtained by the X-ray imaging device 1, performs various processes on the generated reconstructed images and displays the images. The controller 5 performs a grating relative position estimation process described below so as to estimate, from moire fringe images obtained by the X-ray imaging device 1, the position of the second grating 15 at each imaging in fringe scanning.

Figure 4:
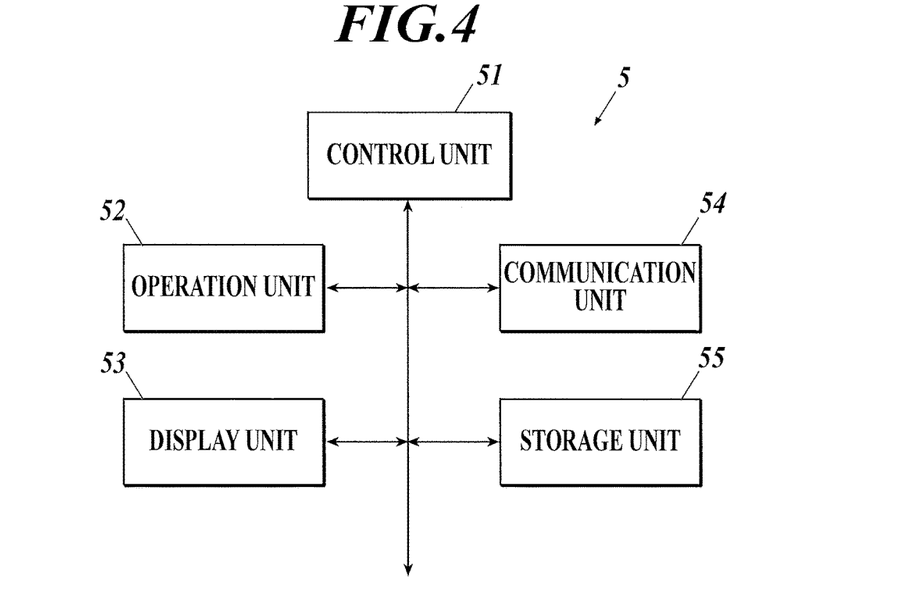
FIG. 4 is a block diagram showing the functional configuration of a controller.

The controller 5 includes, as shown in FIG. 4, a control unit 51, an operation unit 52, a display unit 53, a communication unit 54 and a storage unit 55.

The control unit 51 includes a CPU (Central Processing Unit) and a RAM (Random Access Memory) and performs various processes including the below-described reconstruction process and grating relative position estimation process. The control unit 51 functions as a setting unit, a reconstruction unit and an estimation unit.

The operation unit 52 includes: a keyboard provided with cursor keys, number input keys, various function keys and so forth; and a pointing device such as a mouse, and generates press signals in response to the keys of the keyboard being pressed and operation signals in response to the mouse being operated and outputs the press signals and the operation signals to the control unit 51 as input signals. The operation unit 52 may also include a touch panel integrated into a display of the display unit 53, and generate operation signals in response to the touch panel being operated and output the operation signals to the control unit 51.

The display unit 53 includes a monitor such as a CRT (Cathode Ray tube) or an LCD (Liquid Crystal Display) and displays operation screens, the generated reconstructed images and so forth under display control of the control unit 51.

The communication unit 54 includes a communication interface and communicates with the X-ray imaging device 1 or the X-ray detector 16 on a network with or without a cable. For example, the communication unit 54 sends fringe scanning conditions and control signals to the X-ray imaging device 1 and receives moire fringe images from the X-ray imaging device 1 or the X-ray detector 16.

The storage unit 55 stores therein the programs which are executed by the control unit 51, data necessary for execution of the programs, process results obtained by execution of the programs and so forth.

The storage unit 55 also stores therein the moire fringe images received from the X-ray imaging device 1, the reconstructed images generated on the basis of the moire fringe images and so forth which are correlated with patient information.

[Principles of Talbot Interferometer and Talbot-Lau Interferometer]

Hereinafter, an X-ray imaging method with the Talbot-Lau interferometer of the X-ray imaging device 1 is described.

Figure 5:
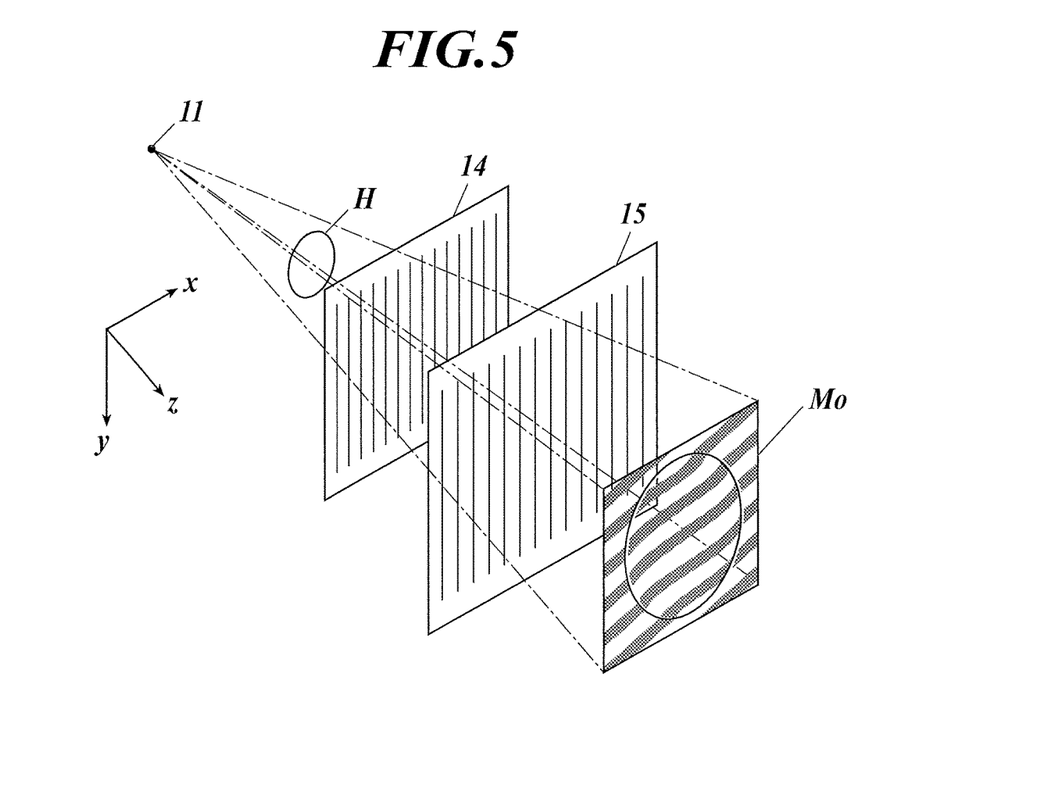
FIG. 5 is an illustration to explain principles of a Talbot interferometer.

As shown in FIG. 5, when the X-rays emitted from the X-ray source 11 pass through the first grating 14, the X-rays having passing through the first grating 14 form an image at constant intervals in the z-direction. These images are called self-images, and phenomenon of self-images being formed is called the Talbot effect. The second grating 15 is arranged at a position where a self-image is formed, in such away as to be approximately parallel to the self-image, and the X-rays having passing through the second grating 15 form a moire fringe image ("Mo" in FIG. 5). That is, the first grating 14 forms an interval pattern, and the second grating 15 converts the interval pattern into moire fringes. When a subject ("H" in FIG. 5) exists between the X-ray source 11 and the first grating 14, the phase of the X-rays is shifted by the subject, so that, as shown in FIG. 5, the moire fringes on the moire fringe image are deformed with the periphery of the subject as a border. This deformation of the moire fringes is detected by processing the moire fringe image so that an image of the subject is formed. This is the principles of a Talbot interferometer.

In the X-ray imaging device 1, the multi-slit 12 is provided near the X-ray source 11 between the X-ray source 11 and the first grating 14, and X-ray imaging with a Talbot-Lau interferometer is performed. A Talbot interferometer is premised on the X-ray source 11 being an ideal point source. However, in the actual X-ray imaging, the X-ray source 11 having a focal point of a large diameter to some extent is used. Then, through the multi-slit 12, the X-ray source 11 acts like a plurality of point sources arranged in a serial row emitting X-rays. This is the X-ray imaging method with a Talbot-Lau interferometer, which demonstrates the same Talbot effect as a Talbot interferometer demonstrates even when the diameter of the focal point is large to some extent.

[Fringe Scanning]

In the X-ray imaging system of the embodiment, the X-ray imaging device 1 performs fringe scanning. The fringe scanning means performing imaging M times (M is a positive integer of more than 2) while moving one of the gratings (the multi-slit 12, the first grating 14 or the second grating 15) in the slit interval direction (x direction), thereby obtaining M moire fringe images. Ideally, moving the grating in the slit interval direction d/M (μm) per time and imaging are alternated, whereby M moire fringe images are obtained, wherein d (μm) represents the slit interval of the grating to be moved.

In the embodiment, the X-ray imaging device 1 performs fringe scanning in which the second grating 15 is moved.

More specifically, in the X-ray imaging device 1, when the exposure switch of the operation unit 182 is pressed by an operator, the control unit 181 performs the fringe scanning control process so as to perform fringe scanning action detailed below. Note that, for example, after the last fringe scanning ends, the drive unit 15a moves the second grating 15 back to its original position, so that the second grating 15 is at approximately the original position when the fringe scanning control process starts.

First, the X-ray source 11 starts emitting X-rays in a state in which the second grating 15 stops. In the X-ray detector 16, after resetting is performed to remove unnecessary electric charges which have remained since the last imaging, electric charges are accumulated in response to the start of the X-ray emission, and the accumulated electric charges are read as image signals in response to the stop of the X-ray emission. This is the $1^{st}$ imaging. At the timing when the $1^{st}$ imaging ends, the second grating 15 starts moving through the drive unit 15a. The second grating 15 stops moving when having moved d/M (in reality, error may be included) (μm), and the next imaging starts. Thus, the second grating 15 alternates moving with stopping, whereby imaging is performed (M−1) times. When the second grating 15 stops, X-rays are emitted and image signals are read. The end of M times, including the first time, of imaging (i.e., the end of the $M^{th}$ imaging) means the end of a series of imaging processes to obtain moire fringe images which are different in a phase of moire fringes and necessary to generate one reconstructed image.

When the fringe scanning ends, the control unit 181 sends the moire fringe images to the controller 5 through the communication unit 184. The communication unit 184 may send the obtained one moire fringe image to the controller 5 each time imaging is performed, or may send all of the M moire fringe images thereto when the $M^{th}$ imaging in the fringe scanning ends.

When sending the moire fringe images to the controller 5 through the communication unit 184, the control unit 181 attaches the fringe scanning conditions (the number of times imaging is performed in fringe scanning "M"; a number of each of the moire fringe image in taken order thereof "k"; the slit interval of the moved second grating 15 "d"; the pixel size of the X-ray detector 16 "D"; the relative angle "θ"; the image type; etc.) to the moire fringe images (for example, by writing them in header information or the like) so as to send the moire fringe images together with the fringe scanning conditions to the controller 5.

In order to obtain a reconstructed image(s) of a subject, fringe scanning in a state in which a subject is placed on the subject table 13 (subject-existing fringe scanning) and fringe scanning in a state in which no subject is placed on the subject table 13 (no-subject-existing fringe scanning) are performed, whereby a series of moire fringe images with a subject included and a series of moire fringe images with no subject included are generated. This is called principal photography. Of these moire fringe images, the moire fringe images with a subject included are called subject moire fringe images, and the moire fringe images with no subject included are called BG moire fringe images. Further, each series of moire fringe images obtained by fringe scanning is called a moire fringe image set.

If the relative angle θ of the second grating 15 to the first grating 14 is changed between the subject-existing fringe scanning and the no-subject-existing fringe scanning of the principal photography, and the gratings are not uniformly manufactured, uneven high frequency due to the gratings may remain in a reconstructed image, and signals derived from the subject may be damaged. Hence, the subject-existing fringe scanning and the no-subject-existing fringe scanning of the principal photography are performed in such a way that a moire fringe interval hardly changes therebetween.

[Reconstruction Process]

In the controller 5, when receiving the subject moire fringe image set and the BG moire fringe image set through the communication unit 54 from the control unit 18, the control unit 51 performs the reconstruction process by working together with a program stored in the storage unit 55 so as to generate reconstructed images, such as a differential phase image, a small-angle scattering image and an X-ray absorption image, on the basis of the received subject moire fringe image set and BG moire fringe image set. Hereinafter, the reconstruction process is described.

As described above, in fringe scanning, one of the gratings (one of the multi-slit 12, the first grating 14 and the second grating 15; in the embodiment, the second grating 15) is moved ideally 1/M (M>2) of the slit interval d of the grating in the slit interval direction each time imaging is performed, whereby M images are obtained. The gratings other than the second grating 15 to be moved are deemed to be still. However, if an environmental condition changes between one fringe scanning and the next fringe scanning, a positional relationship of the second grating 15 and the other gratings in fringe scanning changes. Then, the other gratings, which are still, are deemed to be still at their original positions, and a relative position of the second grating 15, which is moved, at its original position to the gratings, which are still, at their respective original positions (a relative position thereof in the slit interval direction) is put as $\chi_0$.

A relative position of the second grating 15 from its original position (a relative position thereof in the slit interval direction) at each imaging in fringe scanning is expressed by the following Formula 1, wherein $\chi_k$ (k=1, ..., M) represents the relative position of the second grating 15 (grating).

$$\chi_k = \frac{d}{M}(k-1) + \alpha_k \quad \text{[Formula 1]}$$

In Formula 1, d represents the slit interval of the second grating 15, which is moved in fringe scanning, and $\alpha_k$ represents error in the relative position at the $k^{th}$ imaging for the $k^{th}$ image.

As described above, in the Talbot interferometer or Talbot-Lau interferometer, moire fringe images are formed by the self-image of the first grating 14 and the second grating 15. In general, when the slit interval of the self-image of the first grating 14 matches the slit interval of the second grating 15, a moire fringe intensity $I_k(x,y)$ detected at a pixel (x,y) of the X-ray detector 16 is expressed by the following Formula 2.

$$I_k(x,y) = a_0(x,y) + \sum a_n(x,y)\exp\left[2\pi ni\left(\frac{Dy\theta}{d_2} + \frac{\chi_0 + \chi_k}{d}\right)\right] \quad \text{[Formula 2]}$$

In Formula 2, D represents the pixel size of the X-ray detector 16, $d_2$ represents the slit interval of the self-image of the first grating 14 and the second grating 15, θ represents the relative angle (rad) of the second grating 15 to the first grating 14 in the case where the slits of the first grating 14 are arranged in parallel to a y axis (direction), $\alpha_n$ (n is not 0 but an integer; n=1, 2, ...) represents ½ of the amplitude of a moire fringe component having an interval of $d_2/n\theta$ (μm) produced by the moire fringe intensity $I_k(x,y)$ subjected to discrete Fourier transform, and $\alpha_0$ represents a direct current component which is the average value of the moire intensity $I_k(x,y)$. Formula 2 expresses the moire fringe intensity in the case of no subject.

In the actual Talbot interferometer or Talbot-Lau interferometer, the higher order (n>2) component can be ignored by setting an appropriate number of times fringe scanning is performed. That is, Formula 2, which expresses distribution of moire fringe intensities, can be approximated by the following Formula 3.

$$I_k(x,y) \approx a_0(x,y) + 2a_1(x,y)\cos 2\pi\left(\frac{Dy\theta}{d_2} + \frac{\chi_0 + \chi_k}{d}\right) \quad \text{[Formula 3]}$$
$$= b_0(x,y) + b_1(x,y)\cos(\varphi(x,y) + \delta_k)$$

In Formula 3, $$\varphi(x,y) = 2\pi\left(\frac{Dy\theta}{d_2} + \frac{\chi_0}{d}\right) \quad \text{[Formula 4]}$$

and $$\delta_k = 2\pi\frac{d(k-1)/M + \alpha_k}{d}. \quad \text{[Formula 5]}$$

In the above formulae, $\delta_k$ represents a phase change of moire fringes caused by one of the gratings being moved to the relative position $\chi_k$.

In the reconstruction process, the parameters $b_0(x,y)$, $b_1(x,y)$ and $\phi(x,y)$ which constitute Formula 3 are extracted from M moire fringe images, and a differential phase image, an X-ray absorption image and a small-angle scattering image are generated as reconstructed images.

Formula 3 can be expressed as the following Formula 6.

$$I_k(x,y) = c_0(x,y) + c_1(x,y)\cos\delta_k + c_2(x,y)\sin\delta_k$$

provided that $c_0(x,y) = b_0(x,y)$, $c_1(x,y) = b_1(x,y)\cos\phi(x,y)$, and $c_2(x,y) = -b_1(x,y)\sin\phi(x,y)$ [Formula 6]

When $\delta_k$ is known, the parameters $c_0(x,y)$, $c_1(x,y)$ and $c_2(x,y)$ to minimize difference between the moire fringe intensity's measured value $I_k'(x,y)$ and the moire fringe intensity's theoretical value $I_k(x,y)$ can be obtained. A method for deriving the parameters $c_0(x,y)$, $c_1(x,y)$ and $c_2(x,y)$ of Formula 6 is described by Toyohiko YATAGAI in "Ouyou Kougaku Hikari Keisoku Niyuumon (Applied Optics, Introduction to Optical Measurement)" (Maruzen Publishing Co., Ltd., pp. 131-135, 1988), and only the result is shown herein.

When a matrix C is defined by the following Formula 7, the parameters $c_0(x,y)$, $c_1(x,y)$ and $c_2(x,y)$ can be obtained by the following Formula 8.

$$C = \begin{pmatrix} c_0(x,y) \\ c_1(x,y) \\ c_2(x,y) \end{pmatrix}$$ [Formula 7]

$$c = x^{-1} Y$$ [Formula 8]

In the formulae, $$X = \begin{pmatrix} 1 & \frac{1}{M}\sum_{k=1}^{M}\cos\delta_k & \frac{1}{M}\sum_{k=1}^{M}\sin\delta_k \\ \frac{1}{M}\sum_{k=1}^{M}\cos\delta_k & \frac{1}{M}\sum_{k=1}^{M}\cos^2\delta_k & \frac{1}{M}\sum_{k=1}^{M}\cos\delta_k\sin\delta_k \\ \frac{1}{M}\sum_{k=1}^{M}\sin\delta_k & \frac{1}{M}\sum_{k=1}^{M}\cos\delta_k\sin\delta_k & \frac{1}{M}\sum_{k=1}^{M}\sin^2\delta_k \end{pmatrix}$$ [Formula 9]

$$Y = \begin{pmatrix} \frac{1}{M}\sum_{k=1}^{M} I_k'(x,y) \\ \frac{1}{M}\sum_{k=1}^{m} I_k'(x,y)\cos\delta_k \\ \frac{1}{M}\sum_{k=1}^{M} I_k'(x,y)\sin\delta_k \end{pmatrix}$$ [Formula 10]

With the parameters $c_0(x,y)$, $c_1(x,y)$ and $c_2(x,y)$ obtained by Formula 8, the parameters $b_0(x,y)$, $b_1(x,y)$ and $\phi(x,y)$ can be obtained as shown below.

$b_0(x,y) = c_0(x,y)$ [Formula 11]

$b_1(x,y) = \sqrt{c_1^2(x,y) + c_2^2(x,y)}$ [Formula 12]

$$\varphi(x,y) = -\tan^{-1}\frac{c_2(x,y)}{c_1(x,y)}$$ [Formula 13]

An X-ray absorption image $I_{ATT}(x,y)$, a small-angle scattering image $I_{SAS}(x,y)$ and a differential phase image $I_{DPC}(x,y)$ can be calculated by the following Formula 14, Formula 15 and Formula 16 (or Formula 17), respectively, with the parameters obtained from the subject moire fringe image set, $b_{0,sample}(x,y)$, $b_{1,sample}(x,y)$, $\phi_{sample}(x,y)$, $c_{1,sample}(x,y)$ and $c_{2,sample}(x,y)$, and the parameters obtained from the BG moire fringe image set, $b_{0,BG}(x,y)$, $b_{1,BG}(x,y)$, $\phi_{BG}(x,y)$, $c_{1,BG}(x,y)$ and $c_{2,BG}(x,y)$.

$$I_{ATT}(x,y) = \frac{b_{0,sample}(x,y)}{b_{0,BG}(x,y)}$$ [Formula 14]

$$I_{SAS}(x,y) = \frac{b_{1,sample}(x,y)/b_{0,sample}(x,y)}{b_{1,BG(x,y)}/b_{0,BG}(x,y)}$$ [Formula 15]

The differential phase image $I_{DPG}(x,y)$ can be calculated by $$I_{DPC}(x,y) = \frac{1}{\pi}(\varphi_{sample}(x,y) - \varphi_{BG}(x,y))$$ [Formula 16]

but may be calculated by $$I_{DPC}(x,y) = -\frac{1}{\pi}\tan^{-1}\frac{c_{2,samle}(x,y)c_{1,BG}(x,y) - c_{2,BG}(x,y)c_{1,sample}(x,y)}{c_{1,sample}(x,y)c_{1,BG}(x,y) + c_{2,sample}(x,y)c_{2,BG}(x,y)}.$$ [Formula 17]

That is, in the reconstruction process, the X-ray absorption image $I_{ATT}(x,y)$, the small-angle scattering image $I_{SAS}(x,y)$ and the differential phase image $I_{DPC}(x,y)$ are calculated on the basis of the moire fringe intensity $I_k'(x,y)$ of the subject moire fringe images and the moire fringe intensity $I_k'(x,y)$ of the BG moire fringe images and the relative position $\chi_k$ of the second grating 15 at the $k^{th}$ imaging in fringe scanning. Hence, in order to perform the reconstruction process, the control unit 51 needs to set the relative position $\chi_k$ of the second grating 15 at the $k^{th}$ imaging in the fringe scanning as a parameter in advance.

In the embodiment, in terms of easiness of data handling, the value of each pixel of the differential phase image is defined by Formula 17, and values which each pixel of the differential phase image can take are from −1 to 1 (or from 0 to 2). When the value of each pixel of the differential phase image is defined by a value in accordance with a physical quantity of a subject, a coefficient determined by, for example, the X-ray energy, the slit interval and/or the subject's position is added to Formula 17.

[Estimation of Relative Position]

As described above, in order to perform the reconstruction process, the relative position $\chi_k$ of the second grating 15 at the $k^{th}$ imaging in fringe scanning needs to be set as a parameter (parameter $\chi_k$). However, when the actual relative position $\chi_k$ of the grating in fringe scanning does not match the set parameter $\chi_k$, artifacts are generated in a reconstructed image owing to the moire fringes produced in the fringe scanning. Then, there has been proposed to detect the relative position $\chi_k$ in fringe scanning with a sensor and set this detected relative position $\chi_k$ as the parameter $\chi_k$. However, this requires a high precision sensor, which is costly.

The above-described reconstruction process includes, as shown in Formulae 14 to 16, an offset process of dividing the value of each pixel of the subject moire fringe image(s) by the value of its corresponding pixel of the BD moire fringe image(s) or subtracting the value of each pixel of the BD moire fringe image(s) from the value of its corresponding pixel of the subject moire fringe image(s). Hence, suppose existence/nonexistence of a subject and the fringe scanning conditions were exactly the same in the imaging (fringe scanning) of the subject moire fringe image(s) and the imaging (fringe scanning) of the BG moire fringe image (s), possible error in the relative position $\chi_k$ in the fringe scanning cannot be detected in the reconstructed image having subjected to the offset process because of the dividing or subtracting of the offset process. Then, the inventor of this application has found out that the relative position $\chi_k$ of the grating at the $k^{th}$ imaging in fringe scanning can be estimated by (i) performing the reconstruction process using moire fringe image sets which are intentionally taken under the different fringe scanning conditions, in particular, to make the moire fringe interval different, so as to generate a reconstructed image(s) in which clear artifacts exist, and (ii) obtaining the parameter $\chi_k$, which is used in the reconstruction process, to minimize the artifacts.

Hereinafter, a sequence of steps from the imaging (fringe scanning) to the grating relative position estimation process to estimate the relative position $\chi_k$ of the second grating 15 in fringe scanning is described with reference to FIG. 6.

First, in the X-ray imaging device 1, fringe scanning is performed so that the moire fringe interval becomes a certain one, whereby one set of moire fringe images (M moire fringe images) is obtained as a moire fringe image set 1 (Step S1). The image data of the obtained moire fringe image set 1 are sent to the controller 5 through the communication unit 184.

Next, in the X-ray imaging device 1, the relative angle θ of the second grating 15 to the first grating 14 is changed by adjusting the relative angle adjustment unit 15b, so that fringe scanning is performed with the relative angle θ different from that used at Step S1, whereby another set of moire fringe images (M moire fringe images) is obtained as a moire fringe image set 2 (Step S2). The image data of the obtained moire fringe image set 2 are sent to the controller 5 through the communication unit 184.

The moire fringe interval can be changed by changing the relative angle θ of the second grating 15 to the first grating 14 as shown in Formula 3. It is preferable that nothing be changed between the fringe scanning at Step S1 and the fringe scanning at Step S2 except the moire fringe interval. A subject H may or may not be placed in each of the fringe scanning at Step S1 and the fringe scanning at Step S2, but no subject H placed is desired.

Figure 7:
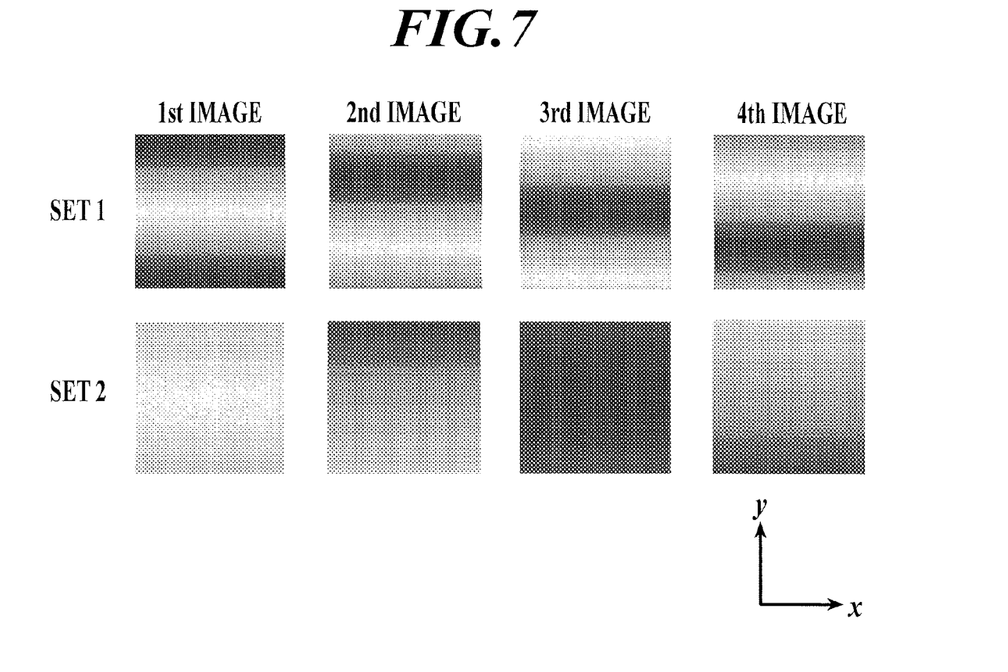
FIG. 7 shows an example of a moire fringe image set 1 and a moire fringe image set 2 which are different in a moire fringe interval, the moire fringe image sets 1 and 2 being generated by a simulation.

FIG. 7 shows an example of the moire fringe image set 1 and the moire fringe image set 2 which are different in the moire fringe interval, the moire fringe image sets 1 and 2 being generated by a simulation.

The moire fringe image sets 1 and 2 shown in FIG. 7 are images calculated by performing a simulation under the following conditions.

Distance D3 from Multi-slit 12 to First Grating 14: 1,107 mm

Distance D3+D4 from Multi-slit 12 to Second Grating 15: 1,364 mm

Multi-slit 12: Slit Interval; 22.8 μm, Slit Width; 6 μm
First Grating 14: Slit Interval; 4.3 μm, Slit Width; 2.15 μm
Second Grating 15: Slit Interval; 5.3 μm, Slit Width; 2.65 μm Pixel Size: 85 μm
Relative Angle θ of Second Grating 15 to First Grating 14: 0.02° and 0.005°
Image Size: 200 pixels×200 pixels In each fringe scanning, imaging is performed four times with the second grating 15 being moved. The relative position $\chi_k$ of the second grating 15 is common to the moire fringe image sets 1 and 2, wherein $\chi_1$=0, $\chi_2$=(0.25+0.005)d, $\chi_3$=(0.5−0.01)d, and $\chi_4$=(0.75+0.005)d.

Next, in the controller 5, the control unit 51 performs the grating relative position estimation process using the moire fringe image sets 1 and 2 so as to estimate the relative position $\chi_k$ of the second grating 15 at the $k^{th}$ imaging in fringe scanning. More specifically, the following Steps S3 to S8 are performed.

First, the control unit 51 sets the parameter $\chi_k$ which indicates the relative position $\chi_k$ of the grating (second grating 15) moved in the fringe scanning (parameter $\chi_k$ which is set as the relative position $\chi_k$ and used in the reconstruction process) at the initial value (Step S3).

The relative position $\chi_k$ (k=1, . . . , M) of the second grating 15 is expressed by Formula 1, and this is the numerator in $\delta_k$ expressed by Formula 5. The relative position $\chi_1$ at the $1^{st}$ imaging for the $1^{st}$ image is $\alpha_1$. This may be deemed to be a constant term, and as $$\chi_k = d(k-1)/M + (\alpha_k - \alpha_1), \qquad \text{[Formula 18]}$$

$$\delta_k = 2\pi \frac{\chi_k}{d} \qquad \text{[Formula 19]}$$

and $$\varphi(x, y) = 2\pi \left( \frac{Dy\theta}{d_2} + \frac{\chi_0 + \alpha_1}{d} \right), \qquad \text{[Formula 20]}$$

the relative position $\chi_k$ of the second grating 15 at the $k^{th}$ imaging in fringe scanning may be re-defined as a relative position with respect to the grating position $\chi_1$ at the $1^{st}$ imaging for the $1^{st}$ image.

When the relative position $\chi_k$ of the second grating 15 at the $k^{th}$ imaging in fringe scanning is defined as a relative position with respect to the grating position $\chi_1$ at the $1^{st}$ imaging for the $1^{st}$ image, the parameter $\chi_1$, which is the parameter $\chi_k$ in the case of k=1, is 0. Hence, when M images are to be taken, parameters for (M−1) times of imaging are to be set.

TABLE 1 below shows an example of the parameter $\chi_k$ for the relative position in the case of M=4.

TABLE 1

| PARAMETER SET | MOIRE FRINGE IMAGE SET 1 | | | | MOIRE FRINGE IMAGE SET 2 | | | |
|---|---|---|---|---|---|---|---|---|
| | 1st IMAGE | 2nd IMAGE | 3rd IMAGE | 4th IMAGE | 1st IMAGE | 2nd IMAGE | 3rd IMAGE | 4th IMAGE |
| 1 | (0) | $x_2$ | $x_3$ | $x_4$ | (0) | $x_2$ | $x_3$ | $x_4$ |
| 2 | (0) | $x_{2\_1}$ | $x_{3\_1}$ | $x_{4\_1}$ | (0) | $x_{2\_2}$ | $x_{3\_2}$ | $x_{4\_2}$ |

In the case where the fringe scanning at Step S1 and the fringe scanning at Step S2 are performed under the same environmental condition, for example, in the case where the moire fringe image sets 1 and 2 are continuously taken, change of the relative position due to the movement of the grating in the fringe scanning can be deemed to be common to the fringe scanning of these two sets. In this case, the parameters to obtain can be a parameter set 1 which is common to the moire fringe image sets 1 and 2. On the other hand, in the case where the fringe scanning at Step S1 and the fringe scanning at Step S2 are not performed under the same environmental condition, for example, in the case where the fringe scanning at Step S1 and the fringe scanning at Step S2 are apart from each other in terms of time and consequently a temperature condition changes, the parameters to obtain are a parameter set 2 in which parameters for the relative positions at the $2^{nd}$ imaging to the $4^{th}$ imaging are different between the moire fringe image sets 1 and 2. The following explanation is made with the parameter set 1 shown in TABLE 1 as an example.

By the way, by setting the relative position $\chi_1$ of the grating, which is the relative position $\chi_k$ in the case of k=1, at 0, the error $\alpha_1$ in the position of the second grating 15 at the $1^{st}$ imaging is reflected on $\phi(x,y)$ as shown in Formula 20. When the error $\alpha_1$ is common to the moire fringe image sets 1 and 2, the error $\alpha_1$ does not affect the differential phase image calculated by Formula 16. Even when the error $\alpha_1$ is not common to the moire fringe image sets 1 and 2, giving consideration to the error $\alpha_1$ is unnecessary because this error $\alpha_1$ is eliminated or attenuated by the below-described correction process on the differential phase image.

In the X-ray imaging device 1, it is set that the second grating 15 is moved 1/M×d per time in fringe scanning. Hence, in the case of M=4, the initial value of the parameter $\chi_k$ set at Step S3 can be common to the moire fringe image sets 1 and 2 as shown in TABLE 2.

TABLE 2

| PARAMETER SET | MOIRE FRINGE IMAGE SET 1 | | | | MOIRE FRINGE IMAGE SET 2 | | | |
|---|---|---|---|---|---|---|---|---|
| | 1st IMAGE | 2nd IMAGE | 3rd IMAGE | 4th IMAGE | 1st IMAGE | 2nd IMAGE | 3rd IMAGE | 4th IMAGE |
| 1 | (0) | 0.25d | 0.5d | 0.75d | (0) | 0.25d | 0.5d | 0.75d |
| 2 | (0) | 0.25d | 0.5d | 0.75d | (0) | 0.25d | 0.5d | 0.75d |

Next, the control unit 51 performs the reconstruction process on the basis of the parameter $\chi_k$ set for the moire fringe image sets 1 and 2 so as to generate reconstructed images (a differential phase image, an X-ray absorption image and a small-angle scattering image) (Step S4).

At Step S4, the parameter $\chi_k$ set at Step S3 and the slit interval d of the second grating 15 are substituted into Formula 19 so that $\delta_k$ is calculated, and an X-ray absorption image, a small-angle scattering image and a differential phase image are generated by Formulae 14, 15 and 17, respectively, with one of the moire fringe image sets 1 and 2 taken as the subject moire fringe image set and the other thereof taken as the BG moire fringe image set.

Figure 8:
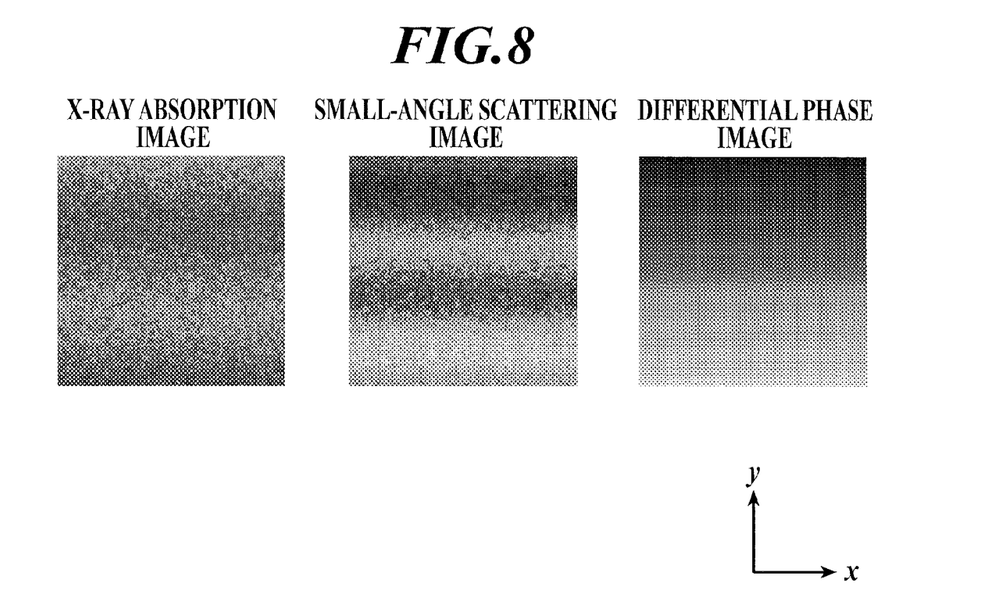
FIG. 8 shows an X-ray absorption image, a small-angle scattering image and a differential phase image generated by setting a parameter $\chi_k$ at the initial value shown in TABLE 2 and performing a reconstruction process using the moire fringe image sets 1 and 2 shown in FIG. 7.

FIG. 8 shows an X-ray absorption image, a small-angle scattering image and a differential phase image generated by setting the parameter $\chi_k$ at the initial value shown in the parameter set 1 in TABLE 2 and performing the reconstruction process using the moire fringe image sets 1 and 2 shown in FIG. 7. As shown in FIG. 8, in each of the X-ray absorption image and the small-angle scattering image, fringe-shaped artifacts in the y direction are seen, whereas in the differential phase image, fringe-shaped artifacts cannot be seen well, but it is understood from FIG. 7 that the signals gradually change along the y direction in the differential phase image.

The artifacts in the y direction in the differential phase image are, as described in Japanese Patent Application Publication No. 2012-170618, due to the relative angle θ of the second grating 15 to the first grating 14 being different for each of the two moire fringe image sets. The artifacts in the differential phase image due to the relative angle θ being different for each of them are generated, as described in the above-mentioned Japanese Patent Application Publication No. 2012-170618, by phase error expressed by f(x,y)=ax+by+c added to the pixel (x,y). Hence, onto the differential phase image, the correction process of the artifacts is performed by subtracting f(x,y)=ax+by+c from the differential phase image $I_{DPC}(x,y)$.

The values of a, b and c of the formula expressing the phase error can be obtained as follows: set at least three points of the differential phase image as measurement points; obtain coordinates of these points (x1,y1) to (x3,y3) and signal values I1 to I3; and substitute the values into the following Formula 21.

$$a = \frac{(I_1 - I_2)(y_2 - y_3) - (I_2 - I_3)(y_1 - y_2)}{(y_2 - y_3)(x_1 - x_2) - (y_1 - y_2)(x_2 - x_3)}$$ [Formula 21]

$$b = \frac{(I_1 - I_2)(x_2 - x_3) - (I_2 - I_3)(x_1 - x_2)}{(x_2 - x_3)(y_1 - y_2) - (x_1 - x_2)(y_2 - y_3)}$$

$$c = I_1 - ax_1 - by_1$$

The artifacts due to the relative angle θ being different for each of the two moire fringe image sets are generated, as shown in FIG. 8, in the y direction mainly. Hence, the formula subtracted from the differential phase image $I_{DPC}(x,y)$ may be approximated by f(x,y)=by+c(x). When the relative angle θ is known, the slope b in the y direction can be calculated in advance. Therefore, it is possible to subtract f(x,y)=by from the differential phase image $I_{DPC}(x,y)$, and thereafter calculate the average c(x) of pixel values in the y direction with respect to each x coordinate of the corrected differential phase image $I_{DPC}(x,y)$ and subtract the calculated c(x) therefrom.

Further, depending on the magnitude of the relative angle θ, discontinuity may occur in the plane of the differential phase image $I_{DPC}(x,y)$ approximately in parallel to the x axis. This is because the differential phase image $I_{DPC}(x,y)$ can take only values in the range from −1 to 1, values outside this range are reflected to be −1 to 1. In this case, it is possible to add a value of "2×an integer" to the differential phase image $I_{DPC}(x,y)$ so as to be continuous in the y direction, and thereafter perform the above correction process. Alternatively, it is possible to subtract f(x,y)=by from the differential phase image $I_{DPC}(x,y)$, and thereafter add a value of "2×an integer" to the differential phase image $I_{DPC}(x,y)$ so as to be continuous in the y direction, and calculate the average c(x) of pixel values in the y direction with respect to each x coordinate of the differential phase image $I_{DPC}(x,y)$ and subtract the calculated c(x) therefrom.

Figure 9:
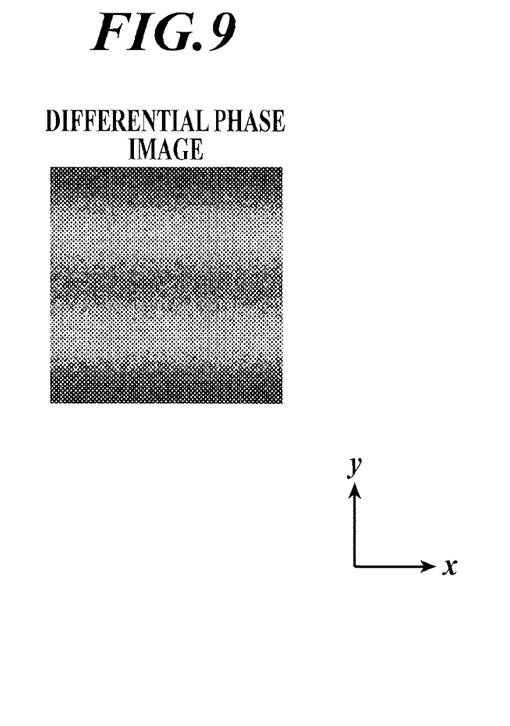
FIG. 9 shows an image obtained by performing a correction process on the differential phase image shown in FIG. 8.

FIG. 9 shows a differential phase image calculated by performing the above correction process on the differential phase image shown in FIG. 8. By performing the correction process of the artifacts due to the relative angle θ being different for each of the two moire fringe image sets on the differential phase image, as shown in FIG. 9, it is understood that fringe-shaped artifacts are generated in the differential phase image too. The X-ray absorption image and the small-angle scattering image shown in FIG. 8 and the differential phase image shown in FIG. 9 are the reconstructed images generated at Step S4.

Next, the control unit 51 calculates a feature amount E (see Formula 22 below) indicating the magnitude of the amplitude of moire fringes on the reconstructed image(s) (Step S5).

Figure 10:
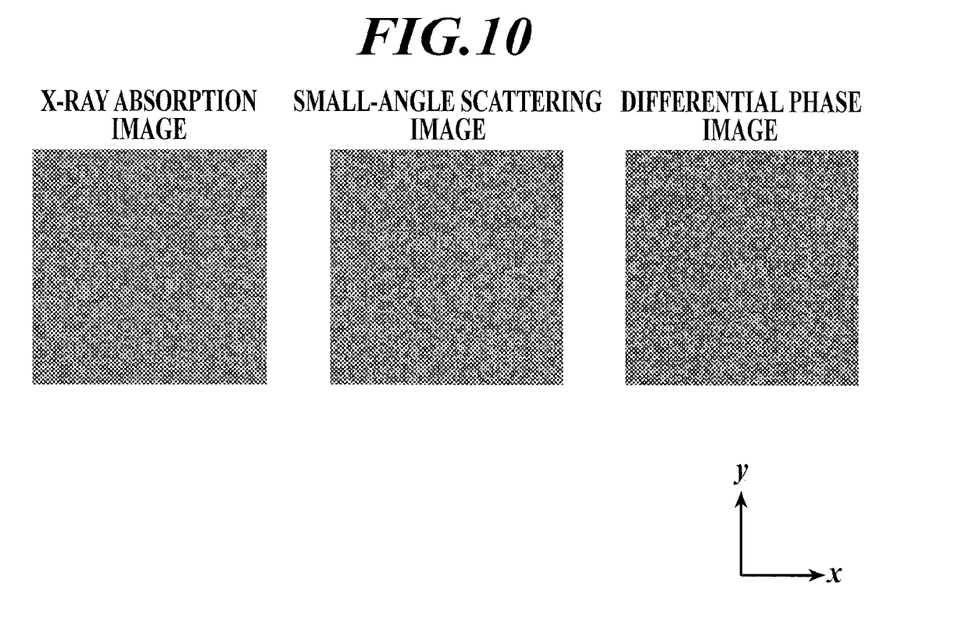
FIG. 10 shows an X-ray absorption image, a small-angle scattering image and a differential phase image generated by performing the reconstruction process with the parameter $\chi_k$ matching the relative position of the second grating at each imaging in fringe scanning.

FIG. 10 shows an X-ray absorption image, a small-angle scattering image and a differential phase image generated by setting the relative position of the second grating 15 at each imaging in fringe scanning as $\chi_2$=(0.25+0.005)d, $\chi_3$=(0.5−0.01)d, and $\chi_4$=(0.75+0.005)d so as to obtain moire fringe image sets 1 and 2, setting the parameter the same as the relative position of the second grating 15 in the fringe scanning, namely, $\chi_2$=(0.25+0.005)d, $\chi_3$=(0.5−0.01)d, and $\chi_4$=(0.75+0.005)d, and performing the reconstruction process of Step S4.

It is understood from the images shown in FIG. 10 that when the reconstruction process is performed by correctly estimating the relative position $\chi_k$ of the second grating 15 in actual measurement (fringe scanning) and setting it as the parameter $\chi_k$, no fringe-shaped artifacts as shown in FIG. 8 or FIG. 9 are generated in a reconstructed image. Therefore, when the parameter $\chi_k$, which is used in the reconstruction process, to make fringe-shaped artifacts as shown in FIG. 8 or 9 sufficiently small, namely, to make the amplitude of moire fringes existing on a reconstructed image sufficiently small, is obtained, this is approximately the relative position $\chi_k$ of the grating in fringe scanning. That is, by obtaining the parameter $\chi_k$ to make the pixel value $I_{ATT}(x,y)$ of the X-ray absorption image, the pixel value $I_{SAS}(x,y)$ of the small-angle scattering image and the pixel value $I_{DPC}(x,y)$ of the differential phase image be target values $I_{ATT}0$, $I_{SAS}0$ and $I_{DPC}0$, respectively, which are provided as constant values within the image data range for evaluation, this can be estimated to be the relative position $\chi_k$ in fringe scanning. More specifically, by obtaining the parameter $\chi_k$ to minimize the feature amount E, which is expressed by the following Formula 22 and indicates the magnitude of the amplitude of moire fringes on a reconstructed image, the relative position $\chi_k$ of the second grating 15 at the $k^{th}$ imaging in fringe scanning can be estimated. As the image data range used for calculation of the feature amount E, the entire effective field of view of the X-ray imaging device 1 may be used, or only a part of the effective field of view, for example, the center part thereof, may be used.

$$E = W_{ATT} \sum_{x,y} (I_{ATT}(x, y) - I_{ATT}0)^2 +$$ [Formula 22]

-continued
$$W_{SAS} \sum_{x,y} (I_{SAS}(x, y) - I_{SAS}0)^2 +$$

$$W_{DPC} \sum_{x,y} (I_{DPC}(x, y) - I_{DPC}0)^2$$

In Formula 22, $W_{ATT}$, $W_{SAS}$ and $W_{DPC}$ represent weights to the X-ray absorption image, the small-angle scattering image and the differential phase image, respectively. As $I_{ATT}0$ and $I_{SAS}0$, constants in accordance with the relative angle θ of the second grating 15 to the first grating 14 and/or a dose condition of the moire fringe image sets 1 and 2 are set, whereas as $I_{DPC}0$, 0 is set because giving consideration to the relative angle θ of the second grating 15 to the first grating 14 is unnecessary (because the artifacts due to the relative angle θ have been corrected). Alternatively, as $I_{ATT}0$, $I_{SAS}0$ and $I_{DPC}0$, the average value of $I_{ATT}(x,y)$, the average value of $I_{SAS}(x,y)$ and the average value of $I_{DPC}(x,y)$ within the image data range used for evaluation may be set, respectively.

At Step S5, the feature amount E is calculated by Formula 22.

Next, the control unit 51 determines whether or not the feature amount E is equal to or less than a predetermined reference value (Step S6). The predetermined reference value is a value predetermined as the minimum value or a sufficiently small value which the feature amount E can take.

When determining that the feature amount E is not equal to or less than the predetermined reference value (Step S6; NO), the control unit 51 changes the parameters $\chi_2$ to $\chi_M$ used in the reconstruction process (Step S7) and returns to Step S4 so as to generate reconstructed images again.

On the other hand, when determining that the feature amount E is equal to or less than the predetermined reference value (Step S6; YES), the control unit 51 estimates the parameters $\chi_2$ to $\chi_M$ used in the reconstruction process at Step S4 to be the relative positions $\chi_2$ to $\chi_M$ of the second grating 15 at the $2^{nd}$ imaging to the $M^{th}$ imaging in fringe scanning, respectively (Step S8).

Regarding minimization of the feature amount E, the minimum value thereof may be obtained by using a general optimization method such as a conjugate gradient method.

The parameters $\chi_2$, $\chi_3$ and $\chi_4$ to minimize the feature amount E are calculated on the basis of the moire fringe image sets 1 and 2 shown in FIG. 7 by using the conjugate gradient method with $W_{ATT}$=$W_{SAS}$=1 and $W_{DPC}$=1 in Formula 22, whereby $\chi_2$=(0.25+0.005+0.0002)d, $\chi_3$=(0.5−0.01+0.003)d, and $\chi_4$=(0.75+0.005+0.0000)d are obtained. The error to the relative positions $\chi_2$, $\chi_3$ and $\chi_4$ in the actual fringe scanning is obtained in 0.1% or less of the interval. Thus, it is understood that use of this method can well estimate the relative position of the second grating 15 at each imaging in fringe scanning. Because the simulation is performed with no difference given to the moire fringe image sets 1 and 2, for the X-ray absorption image and the small-angle scattering image, $I_{ATT}0$=$I_{SAS}0$=1 is set, and $I_{DPC}0$=0 is also set.

Figure 6:
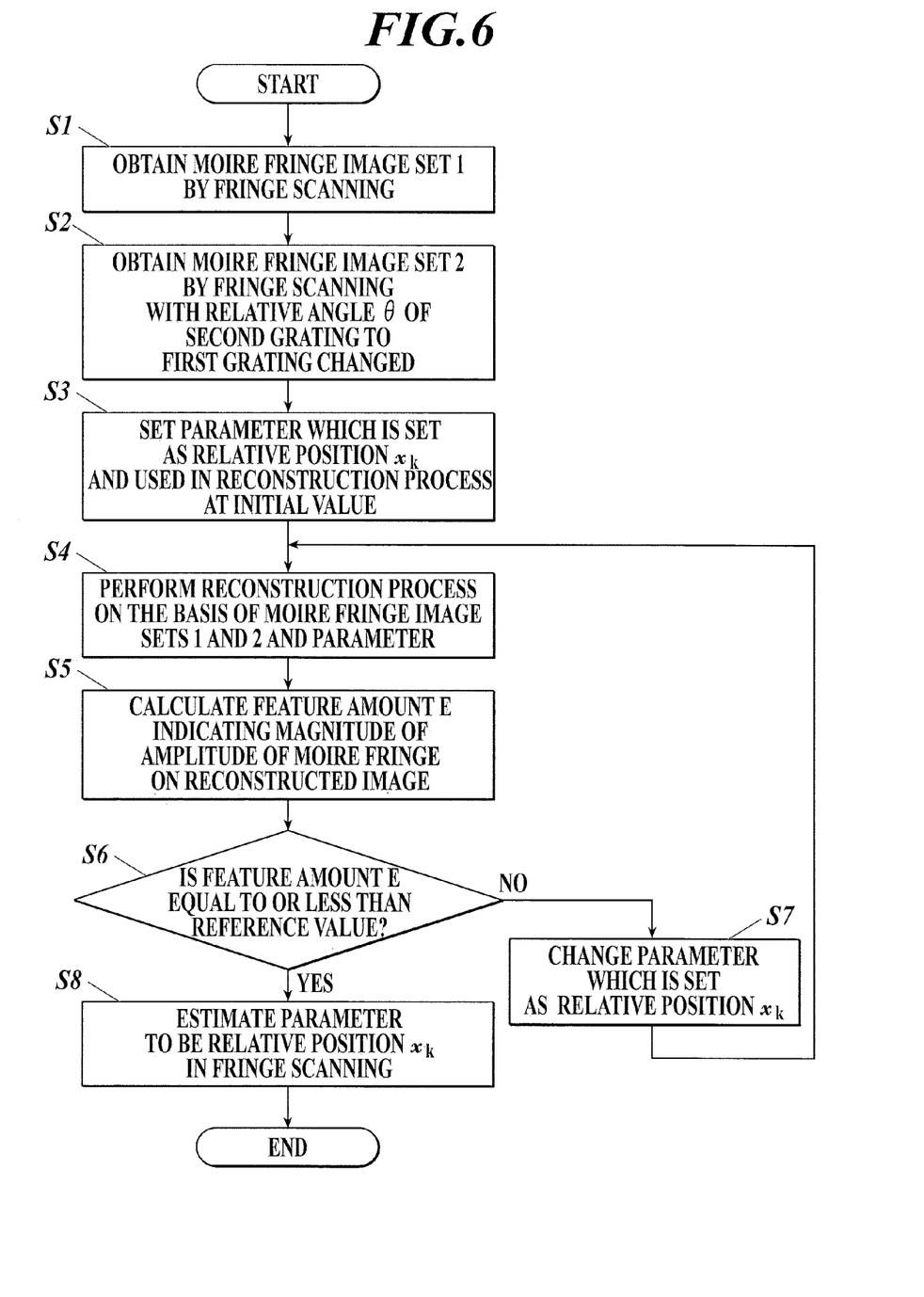
FIG. 6 is a flowchart showing a sequence of steps from imaging (fringe scanning) to image processing (a grating relative position estimation process) to estimate a relative position of a second grating in fringe scanning.

Thus, in the X-ray imaging system, by performing the sequence of the steps from the imaging (fringe scanning) to the grating relative position estimation process shown in FIG. 6, the relative position of the second grating 15 at each imaging in fringe scanning can be estimated from the reconstructed images with high accuracy. Therefore, without adding a special sensor to detect the relative position of a grating moved in fringe scanning to the X-ray imaging device, image degradation due to error in the relative position of the grating can be prevented at low cost.

In the above, the relative position of the grating is estimated by using all three types of reconstructed images, namely, the X-ray absorption image, the small-angle scattering image and the differential phase image. However, as shown in FIG. 8 and FIG. 9, the interval of fringe-shaped artifacts in a reconstructed image depends on the type of the reconstructed image. The X-ray absorption image has therein the fringe-shaped artifacts having the interval twice as large as that of the fringe-shaped artifacts in the differential phase image or the small-angle scattering image. This indicates that influences of the error in the relative position of the grating on the physical quantities derived from the average value component and the amplitude component of moire fringes are different. Actually, as shown in Formula 15, both the average value component and the amplitude component of moire fringes affect the small-angle scattering image. Hence, for estimation of the relative position of the grating, only the small-angle scattering image may be used. That is, the feature amount E may be calculated by Formula 22 with $W_{ATT}=W_{DPD}=0$ and $W_{SAS}=1$. Thus, when the parameters $\chi_2$, $\chi_3$ and $\chi_4$ to minimize the feature amount E are calculated on the basis of the moire fringe image sets 1 and 2 shown in FIG. 7 by using the conjugate gradient method, $\chi_2=(0.25+0.005+0.0002)d$, $\chi_3=(0.50-0.01+0.0007)d$, and $\chi_4=(0.75+0.005+0.0004)d$ are obtained. It is understood therefrom that the relative positions $\chi_2$, $\chi_3$ and $\chi_4$ in fringe scanning are well reproduced. This method can shorten the process time necessary for estimation of the relative position of the grating.

Thus, by obtaining the parameter $\chi_k$ to minimize the amplitude of fringe-shaped artifacts in a reconstructed image based on moire fringe image sets which are different in the moire fringe interval, the relative position of the second grating 15 in actual fringe scanning can be perceived with high accuracy. Hence, although it is detailed below, by adjusting the movement amount of the grating in the X-ray imaging system using the obtained parameter $\chi_k$ in such a way that the error $(\alpha_k-\alpha_1)$ in the relative position becomes 0 or by performing the reconstruction process using the obtained parameter $\chi_k$, the principal photography can be performed with high accuracy.

Further, in the above, the case where the parameter $\chi_k$ is common to the moire fringe image sets 1 and 2 is described. However, to the case where the parameter $\chi_k$ is not common to the moire fringe image sets 1 and 2, such as the parameter set 2 in TABLE 1, too, the same processes apply. Note that, in the reconstruction process to generate a reconstructed image(s) of a subject, the reconstructed image is generated by using the parameters for the moire fringe image set 1 or 2, whichever is taken in an environment similar to that of the principal photography by which signals of the subject are obtained. For example, if the moire fringe image set 1 is taken in the morning and the moire fringe image set 2 is taken right before the principal photography, the principal photography is performed in an environment more similar to the environment of the fringe scanning of the moire fringe image set 2 than the environment of the fringe scanning of the moire fringe image set 1, so that the reconstructed image of the subject is generated by using the parameter $\chi_k$ for the moire fringe image set 2. In the case where the parameter $\chi_k$ is not common to the moire fringe image sets 1 and 2, it is desired that, in the moire fringe image sets 1 and 2, a region where the phase of moire fringes changes about $\pi$ (about half the interval) is included in the image region used for evaluation to calculate the relative position of the grating, because a wide (large) moire fringe interval decreases calculation accuracy of the relative position of the grating. Further, in the case where the parameter $\chi_k$ is not common to the moire fringe image sets 1 and 2, the parameter $\chi_k$ for the moire fringe image set 1 or 2, whichever has a smaller moire fringe interval, is obtained with higher accuracy. Hence, when the environment of the principal photography is more similar to the environment of the fringe scanning of the moire fringe image set 2 than the environment of the fringe scanning of the moire fringe image set 1, it is desired to adjust the relative angle θ of the second grating 15 to the first grating 14 in such a way that the moire fringe interval of the moire fringe image set 2 becomes smaller than that of the moire fringe image set 1.

Further, in the above, in order to change the moire fringe interval between the moire fringe image sets, the relative position θ of the second grating 15 to the first grating 14 is changed. Alternatively, one of the gratings may be moved in the z direction so as to produce moire fringes in parallel to the x direction. In this case too, the relative position $\chi_k$ of the grating can be estimated in the above-described way.

[Feedback of Estimated Relative Position]

Hereinafter, described is a method for feeding back the estimated relative position $\chi_k$ to generate a reconstructed image(s) of a subject.

(Adjustment of Movement Amount of Grating in X-Ray Imaging Device 1)

Before the principal photography, the relative position $\chi_k$ of the grating is estimated (the imaging (fringe scanning) of two moire fringe image sets and the grating relative position estimation process are performed), which is described with reference to FIG. 6, and the control unit 51 of the controller 5 sends the estimated relative position $\chi_k$ to the X-ray imaging device 1 through the communication unit 54. When receiving the estimated relative position $\chi_k$ through the communication unit 184, the control unit 181 of the X-ray imaging device 1 calculates the error $(\alpha_k-\alpha_1)$ in the relative position of the second grating 15 from the estimated relative position $\chi_k$, and adjusts distance (the movement amount) to move the second grating 15 in fringe scanning in such a way that the error $(\alpha_k-\alpha_1)$ becomes 0. The control unit 181 functions as an adjustment unit. After the adjustment, in the X-ray imaging device 1, the second grating 15 is moved the adjusted movement amount by the drive unit 15a, whereby the principal photography is performed, and in the controller 5, the reconstruction process is performed on the basis of the obtained subject moire fringe image set and BG moire fringe image set. At the time, the control unit 51 of the controller 5 generates the reconstructed image with $\chi_k=d(k-1)/M$. Consequently, the artifacts due to the relative position $\chi_k$ of the second grating 15 at the $k^{th}$ imaging in fringe scanning not matching the parameter $\chi_k$ which is set and used in the reconstruction process can be prevented from being generated.

When the $(\alpha_k-\alpha_1)$ due to environmental change is estimated to be small, it is possible to perform, at the time of adjustment of the X-ray imaging device 1 performed at predetermined timing, or each time the X-ray imaging device 1 is powered up, the estimation of the relative positon $\chi_k$ shown in FIG. 6 to the adjustment of the distance to move the second grating 15 based on the estimation result and store the value (the adjusted movement amount) in the storage unit 185, and at the time of the principal photography, to perform imaging while moving the second grating 15 through the drive unit 15a on the basis of the movement amount stored in the storage unit 185.

(Reflection of Estimated Relative Position on Grating Position Set for Reconstruction Process)

Before the principal photography, the relative position $\chi_k$ of the grating is estimated (the imaging (fringe scanning) of two moire fringe image sets and the grating relative position estimation process are performed), which is described with reference to FIG. 6, and the estimated relative position $\chi_k$ is stored in the storage unit 55 of the controller 5. In the reconstruction process based on the subject moire fringe image set and the BG moire fringe image set of the principal photography, the control unit 51 generates a reconstructed image(s) by setting the relative position $\chi_k$ stored in the storage unit 55 as the parameter. Consequently, the artifacts due to the relative position $\chi_k$ of the second grating 15 at the $k^{th}$ imaging in fringe scanning not matching the parameter $\chi_k$ which is set and used in the reconstruction process can be prevented from being generated.

By the way, when the X-ray imaging device 1 is booted up, temperature change occurs in the device 1 due to the heat generated thereby, which may change the relative position $\chi_k$ of the second grating 15. Hence, together with the fringe scanning of the subject moire fringe image set and the fringe scanning of the BG moire fringe image set (also called a BG moire fringe image set 1) of the principal photography, fringe scanning of another BG moire fringe image set (called a BG moire fringe image set 2) is performed with the relative angle θ of the second grating 15 to the first grating 14 changed from that used in the fringe scanning of the BG moire fringe set 1. Then, in the controller 5, the control unit 51 performs the grating relative position estimation process on the basis of the BD moire fringe image set of the principal photography and the BD moire fringe image set 2 with the shared parameter $\chi_k$ (the parameter set 1 in TABLE 1), and reflects the estimated relative position $\chi_k$ on the parameter $\chi_k$ which is used in the reconstruction process performed with the subject moire fringe image set and the BD moire fringe image set of the principal photography to generate a reconstructed image(s) of the subject. At the time, it is desired that the relative angle θ is changed by the relative angle adjustment unit 15b in such a way that the moire fringe interval of the BD moire fringe image set 2 becomes shorter than that of the BG moire fringe image set of the principal photography.

For example, the principal photography is performed in a state in which the relative angle θ of the second grating 15 to the first grating 14 is adjusted to extend the moire fringe interval to the maximum. In this case, the fringe scanning of the BG moire fringe image set 2 is performed in a state in which the relative angle θ of the second grating 15 to the first grating 14 is about 0.01° to 0.03° different from that used in the principal photography. When the image data range used for calculation of the feature amount E is 45 mm square in the effective field of view, the slit interval d of the second grating 15 is 5.3 μm, and the moire fringe interval of the BG moire fringe image set of the principal photography is sufficiently large with respect to 45 mm, the BG moire fringe image set 2 is taken in a state in which moire fringes of one to five intervals are produced in the 45 mm square. The phase of moire fringes changes in the range of 0 to $2\pi$. Hence, the parameter $\chi_k$ to minimize the artifacts in a reconstructed image(s) with respect to any possible phase of moire fringes can be calculated by producing moire fringes of one or more intervals in the image data range used for calculation of the feature amount E.

The fringe scanning of the BG moire fringe image set 2 is unnecessary to be performed together with the principal photography. The BG moire fringe image set 2 may be taken in advance and stored in the storage unit 55 of the controller 5. Then, after the principal photography ends, on the basis of the BG moire fringe image set of the principal photography and the BD moire fringe image set 2 stored in the storage unit 55, the grating relative position estimation process shown in FIG. 6 is performed to calculate the parameter set 2 (parameter $\chi_k$ not common to the BG moire fringe image set of the principal photography and the BD moire fringe image set 2 stored in the storage unit 55) in TABLE 1, and the reconstruction process with the BG moire fringe image set of the principal photography is performed with the parameter $\chi_k$ calculated for the BD moire fringe image set of the principal photography used as the relative position $\chi_k$ of the grating. The fringe scanning of the BG moire fringe image set 2 may be performed with a dose lower than that of the principal photography.

In the above, a preferred embodiment of the X-ray imaging system of the present invention is described. However, the embodiment described above is just one preferred example of the present invention, and hence the present invention is not limited thereto.

For example, in the above embodiment, the X-ray imaging device uses the Talbot-Lau interferometer employing the method of moving the second grating 15 relatively to the multi-slit 12 and the first grating 14 in fringe scanning. However, the present invention is also applicable to an X-ray imaging device which uses a Talbot-Lau interferometer employing a method of moving either the multi-slit 12 or the first grating 14. The present invention is also applicable to an X-ray imaging device which uses a Talbot interferometer employing a method of moving one of the first grating 14 and the second grating 15 relatively to the other thereof.

Further, in the above embodiment, three types of reconstructed images are generated. However, the present invention is also applicable to an X-ray imaging device which generates at least one of the differential phase image and the small-angle scattering image as a reconstructed image.

Besides, the detailed configurations and actions of the device and so forth constituting the X-ray imaging system can be appropriately modified without departing from the scope of the present invention.

What is claimed is:

1. An X-ray imaging system comprising:
   an X-ray imaging device with a Talbot interferometer or Talbot-Lau interferometer in which a plurality of gratings are disposed in a line in an X-ray emitting direction and which obtains moire fringe images by fringe scanning in which one of the gratings is moved relatively to the remaining grating, each of the gratings including a plurality of slits disposed in a direction perpendicular to the X-ray emitting direction; and
   an image processing device including a reconstruction unit which generates at least one of a differential phase image, an X-ray absorption image and a small-angle scattering image as a reconstructed image on the basis of the moire fringe images obtained by the X-ray imaging device, wherein
   the x-ray imaging device obtains multiple sets of moire fringe images by the fringe scanning multiple times between which arrangement of the gratings is changed,
   the reconstruction unit of the image processing device generates a reconstructed image on the basis of the sets of the moire fringe images obtained by the x-ray imaging device, and
   the image processing device further includes an estimation unit which estimates, on the basis of the reconstructed image generated by the reconstruction unit, a relative position of the moved grating from a reference position of the grating at each imaging in the fringe scanning.

2. The X-ray imaging system according to claim 1, wherein
the gratings include a first grating which forms an interval pattern and a second grating which converts the interval pattern of the first grating into a moire fringe, and
the x-ray imaging device obtains the multiple sets of the moire fringe images by the fringe scanning the multiple times between which a relative angle of the second grating to the first grating as the arrangement of the grating is changed.

3. The X-ray imaging system according to claim 1, wherein
the image processing device further includes a setting unit which sets a parameter indicating the relative position of the grating,
the reconstruction unit generates the reconstructed image on the basis of the sets of the moire fringe images and the parameter, and
the estimation unit obtains the parameter to make a feature amount indicating an amplitude of a moire fringe on the reconstructed image equal to or less than a predetermined reference value and estimates the obtained parameter to be the relative position of the grating.

4. The X-ray imaging system according to claim 3, wherein the feature amount is a double sum of a difference between a pixel value of each pixel of the reconstructed image and a predetermined target value.

5. The X-ray imaging system according to claim 3, wherein
the setting unit sets the estimated relative position of the grating as the parameter,
the X-ray imaging device obtains a set of subject moire fringe images by the fringe scanning with a subject placed at a subject placement position on an X-ray path and a set of no-subject moire fringe images by the fringe scanning with no subject placed at the subject placement position on the X-ray path, and
the reconstruction unit generates a reconstructed image of the subject on the basis of the parameter, the set of the subject moire fringe images and the set of the no-subject moire fringe images.

6. The X-ray imaging system according to claim 1, wherein the X-ray imaging device further includes an adjustment unit which adjusts a movement amount of the grating in the fringe scanning on the basis of the estimated relative position of the grating.

7. The X-ray imaging system according to claim 1, wherein the estimation unit estimates the relative position of the grating on the basis of a small-angle scattering image generated by the reconstruction unit as the reconstructed image on the basis of the sets of the moire fringe images.

8. An image processing device comprising:
a reconstruction unit which generates at least one of a differential phase image, an X-ray absorption image and a small-angle scattering image as a reconstructed image on the basis of moire fringe images obtained by an X-ray imaging device with a Talbot interferometer or Talbot-Lau interferometer in which a plurality of gratings are disposed in a line in an X-ray emitting direction and which obtains the moire fringe images by fringe scanning in which one of the gratings is moved relatively to the remaining grating, each of the gratings including a plurality of slits disposed in a direction perpendicular to the X-ray emitting direction; and
an estimation unit which estimates, on the basis of a reconstructed image generated by the reconstruction unit on the basis of multiple sets of moire fringe images obtained by the X-ray imaging device by the fringe scanning multiple times between which arrangement of the gratings is changed, a relative position of the moved grating from a reference position of the grating at each imaging in the fringe scanning.

* * * * *